United States Patent [19]

Skakoon et al.

[11] Patent Number: 4,804,368
[45] Date of Patent: Feb. 14, 1989

[54] BATTERY OPERATED MINIATURE SYRINGE INFUSION PUMP AND IMPROVED HALFNUT THEREFOR

[75] Inventors: James G. Skakoon, Melrose; Philip S. Sleeman, Allston, both of Mass.

[73] Assignee: C. R. Bard, Inc., Murray Hill, N.J.

[21] Appl. No.: 88,806

[22] Filed: Aug. 24, 1987

Related U.S. Application Data

[63] Continuation-in-part of Ser. No. 938,550, Dec. 5, 1986, abandoned.

[51] Int. Cl.4 ............................................. A61M 5/20
[52] U.S. Cl. ............................. 604/155; 128/DIG. 1
[58] Field of Search .......................... 128/DIG. 1, 12; 604/131, 154, 155, 245

[56] References Cited

U.S. PATENT DOCUMENTS 2,702,547 2/1955 Glass .................................. 604/155
4,544,369 10/1985 Skakoon et al. ..................... 604/155

Primary Examiner—Dalton L. Truluck
Attorney, Agent, or Firm—Kane, Dalsimer, Sullivan, Kurucz, Levy, Eisele and Richard

[57] ABSTRACT

Drive means for a small, lightweight, easily operated syringe infusion pump. A syringe is secured in a holder and the syringe plunger is moved by a pusher block of the drive means. The pusher block is advanced to the syringe plunger by squeezing a finger tab. This simultaneously decouples the pusher block from the internal drive and opens the antisiphon catch to allow quick and easy set-up. The pusher block is moved by the engagement of a floating halfnut on a threaded leadscrew. A force is applied to the halfnut by the block substantially near the midpoint of the leadscrew thereby greatly reducing force mechanisms that attempt to separate the leadscrew and halfnut. A relatively light first biasing means is on the block for applying a relatively small force between the halfnut and the leadscrew.

9 Claims, 3 Drawing Sheets

BATTERY OPERATED MINIATURE SYRINGE INFUSION PUMP AND IMPROVED HALFNUT THEREFOR

This application is a continuation-in-part of commonly assigned application Ser. No. 938,550 filed Dec. 5, 1986, now abandoned.

REFERENCE TO RELATED PATENTS

This invention relates to an improved battery operated miniature syringe infusion pump of the type disclosed in commonly assigned U.S. Pat. No. 4,544,369 with an improved halfnut/leadscrew assembly therefor, wherein the halfnut is resiliently held against the lead screw.

BACKGROUND OF THE INVENTION

Currently on the market there are syringe infusion pumps that hold drug filled syringes and empty the contents into patients requiring intravenous infusions. Most typically, syringe infusion pump drives are motor driven leadscrew assemblies. Also, for easy resetting of the drive when an emptied syringe is to be replaced with a filled syringe, a halfnut driving nut is typically used. For accurate drug delivery, it is necessary that the drive be fully engaged without slipping under load. Nonetheless, for ease of use by nursing personnel, the drive must be easily decoupled for resetting without excessive force or unusual skill.

Halfnut/leadscrew drive mechanisms for syringe infusion pumps have therefore been used to translate rotary motion to linear motion yet provide convenient drive disengagement if required. Because of their ability to be disengaged by the operator, their design is not necessarily straightforward. They need to be easily disengaged, yet must remain fully engaged under all expected driving conditions.

A guided halfnut of the type disclosed in U.S. Pat. No. 4,544,369 requires a relatively large supplemental engagement force between the halfnut and leadscrew to assure engagement under all conditions. This force is typically supplied by a spring. This spring force must be overcome by the operator during disengagement. Further, the necessary spring force increases with increasing drive loads. Stated another way, the drive load will bring about forces which tend to separate the leadscrew and halfnut, and these forces must be counteracted by an external, supplemental force.

The previously disclosed commercial infusion pumps used a spring loaded halfnut of similar design that was guided with respect to the leadscrew by other components in the assembly. A lever or button was squeezed to effect decoupling. This arrangement required a force of over 4 lbs. to assure that the halfnut remained engaged. This high force proved to be difficult to overcome by nurses. This resulted not only in inconvenience, but also inadvertent product abuse, since the halfnut was often scraped against the leadscrew as the drive assembly was reset.

A jamming halfnut has also been disclosed in the prior art and can be designed such that the drive load causes forces which tend to engage the halfnut with the leadscrew. The geometry of the system is made so that the halfnut/leadscrew reaction and the halfnut/pusher block reaction are equal but opposite Therefore, the separation component of the former is countered by the restoring component of the latter and engagement is maintained.

It was clear that lowering the coupling spring force would improve the product by making it easier to decouple The problem overcome by this invention was how to accomplish this without compromising, and, hopefully, while even improving the drive system's life and drive capability.

Several potential solutions were considered and dismissed. Mechanisms with mechanical advantage could lower the disengagement force required, but needed additional parts and therefore assembly complexity. A pivoting halfnut was very inviting because the halfnut had a self-jamming effect. That is, the drive force resulted in a directly proportional coupling force. Because of this, the spring force could be made virtually zero if the pivot point was properly chosen. It was discovered, however, that while the drive held firmly against the normal drive forces, the drive assembly could too easily be advanced forward over the leadscrew threads if the loads were reversed. This could result in a dangerous drug overdose if the drive assembly was bumped or hit. Further, the drive assembly again required additional complexity.

OBJECTS AND SUMMARY OF THE INVENTION

The present invention recognized that placing the contact points between the pusher block and halfnut near the midpoint of the leadscrew greatly reduces the force mechanisms that attempt to separate the halfnut from the leadscrew. Further, the halfnut is neither guided nor pivoted against the leadscrew as in the prior art, but is allowed to float under the influence of the drive load, spring force, friction forces between the halfnut and leadscrew, and frictional forces between the halfnut and pusher block. A balance of forces was made to exist by properly choosing the contact points among the halfnut, leadscrew, and pusher block, and by allowing the halfnut to float so that leadscrew rotation will not result in net frictional separation forces. This balance of forces resulted in an unconditionally stable mechanical arrangement in which separation can never result from applied drive loads (within material performance characteristics). Nonetheless, drive decoupling could still be accomplished by simple translation of the halfnut perpendicular to the leadscrew.

It is therefore a principal object of the present invention to provide an improved syringe infusion pump for reliable and accurate intravenous administration of the therapeutic agents and drugs such as antibiotics, the improvement in operation resulting from the incorporation of a pusher block assembly with a novel force balanced floating halfnut.

The infusion pump of this invention whereby the foregoing objects are attained will hold and empty a syringe. Its syringe barrel is secured in a snap-in holder and the syringe plunger is moved by a pusher having a halfnut forced against the leadscrew. The pusher is advanced to the syringe plunger during set-up by squeezing a finger tab and sliding the pusher forward. This simultaneously decouples the pusher from the internal drive and opens the antisiphon catch to allow quick and easy set-up. To initiate flow, a switch is moved to the "on" position. The pusher is moved by the engagement of a nut on a threaded leadscrew. The leadscrew is rotated, through appropriate gearing, by a motor. A force sensing system is included as part of the syringe holder and is used to detect end of syringe and occlusion. Visual indicators and audio alarms for infusion and warning and to sense condition of the batteries are provided Other objects and advantages will become apparent from the following detailed description which is to be taken in conjunction with the accompanying drawings.

DETAILED DESCRIPTION

Figure 1:
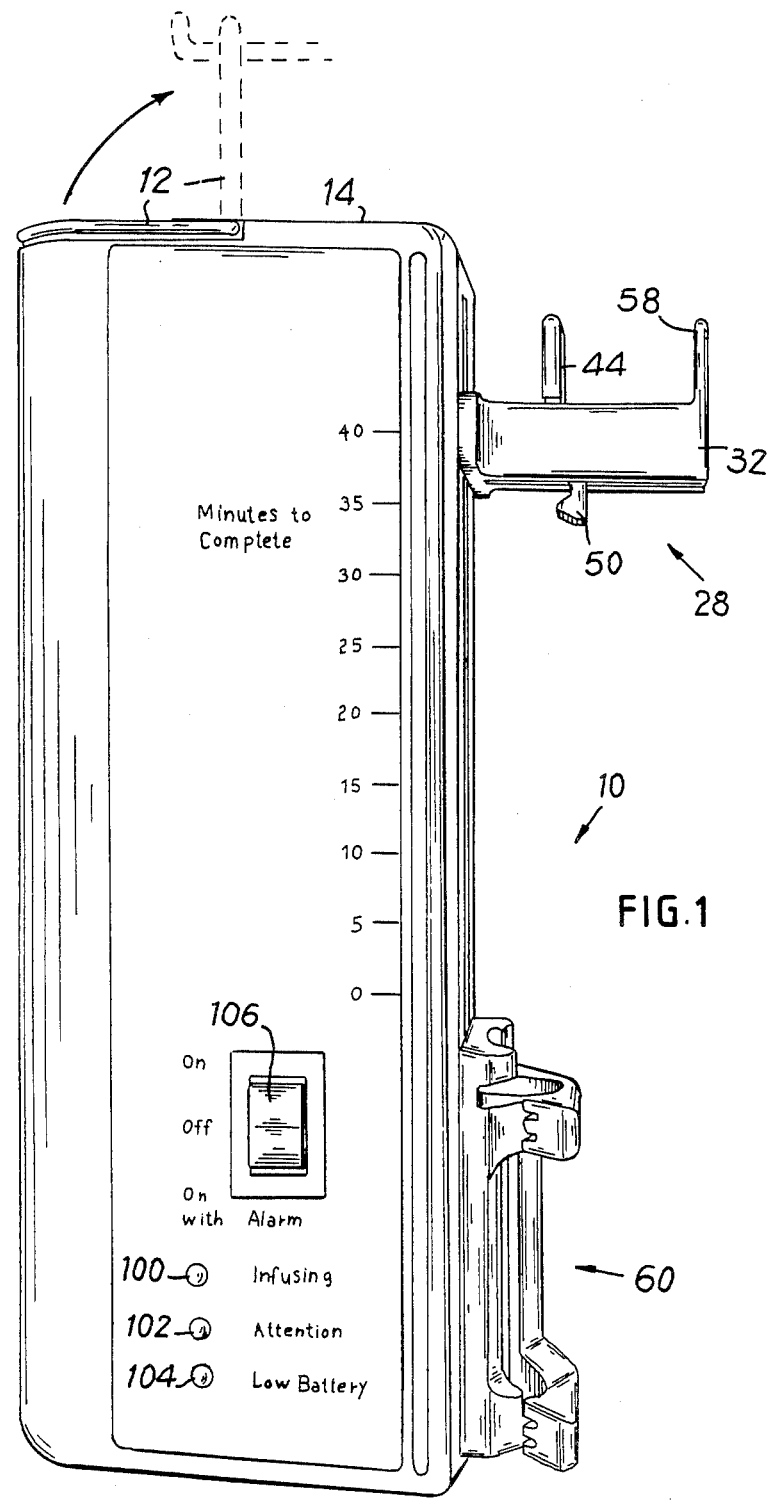
FIG. 1 is a front elevational view of a battery operated syringe infusion pump incorporating the teachings of this invention.
Figure 4:
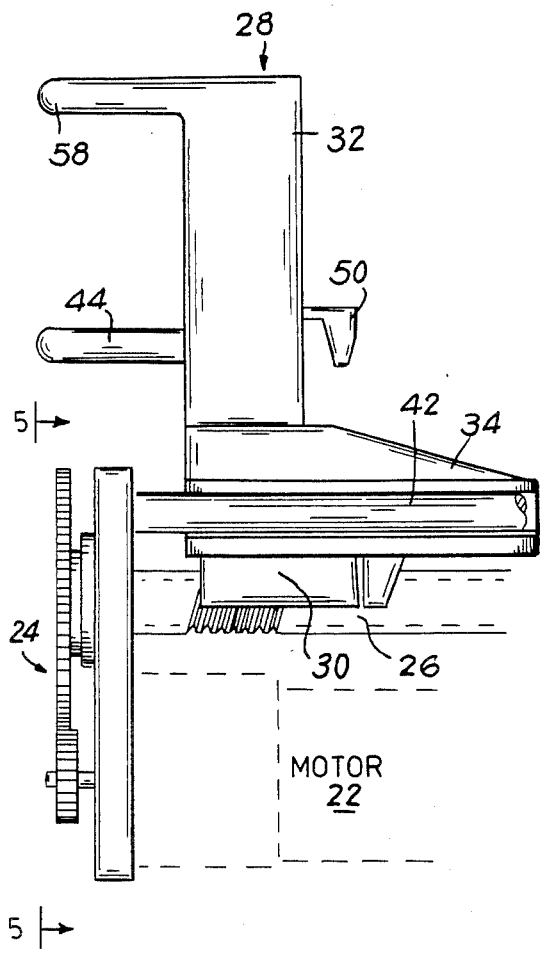
FIG. 4 is an enlarged fragmentary view of the pusher block assembly shown associated with the leadscrew.
Figure 5:
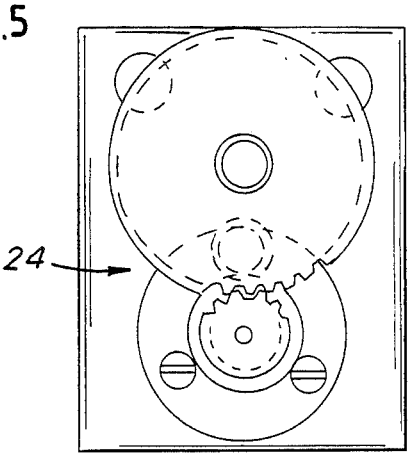
FIG. 5 is an end view of motor gear drive for the leadscrew.

In the drawings, a small, lightweight battery operated syringe infusion pump 10 of this invention is adapted to be hung or suspended from an IV pole or similar conveniently located support by means of attachment loop 12 pivotal between a retracted position and an extended position as shown in FIG. 1. A front cover 14 and a rear cover 16 advantageously houses the internal componentry and defines compartment 18 that conveniently receives the batteries 20 for energizing the fixed and single or multiple speed motor 22. The drive of motor 22 is coupled with gear network 24 which in turn drives the leadscrew 26 as shown in FIGS. 4 and 5.

Figure 2:
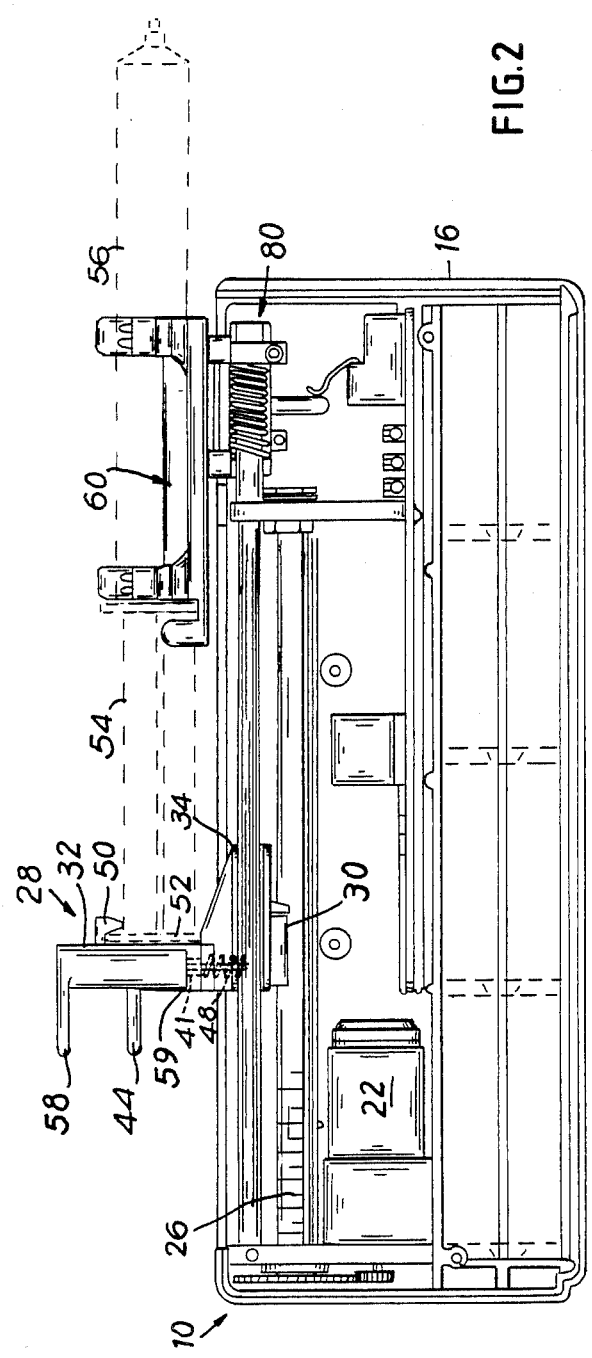
FIG. 2 is a similar front elevational view with the front cover removed.
Figure 3:
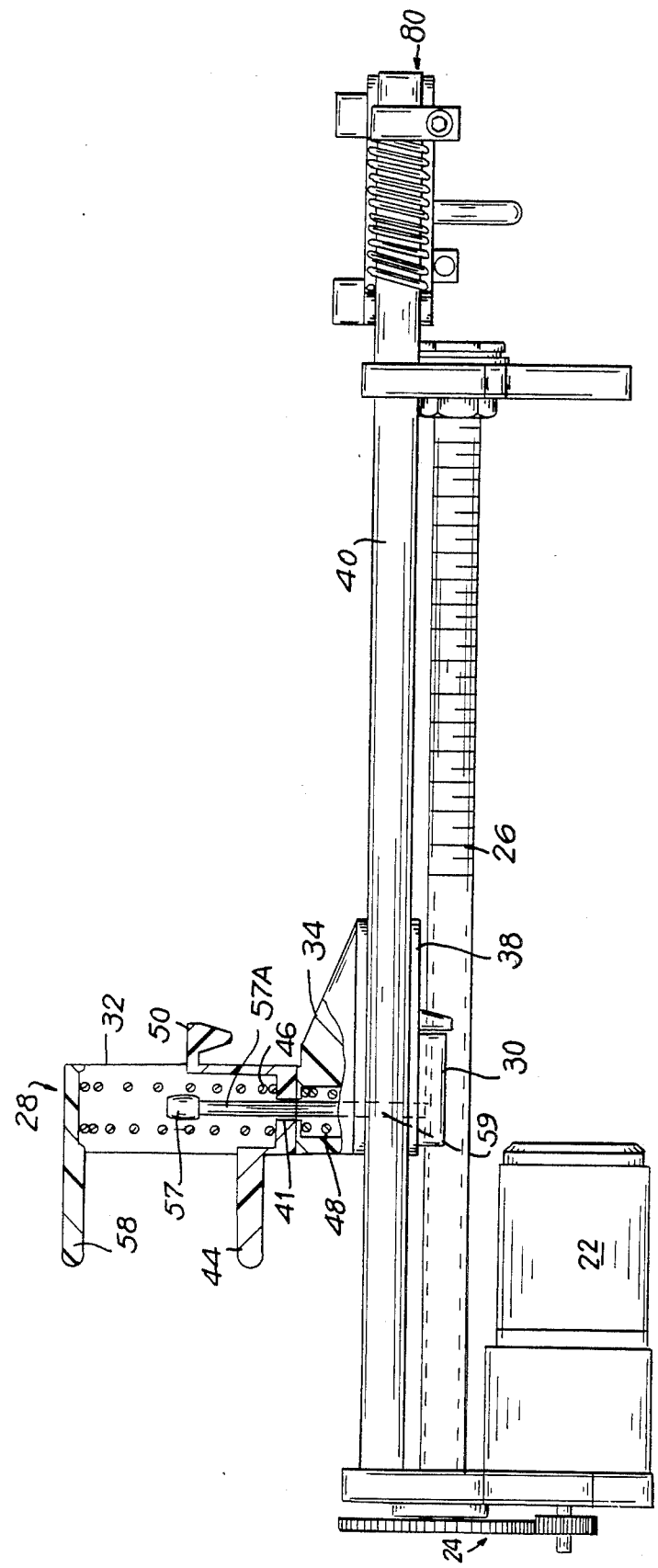
FIG. 3 is an enlarged side elevational view of the pusher block assembly with certain parts broken away, removed and sectioned.

A pusher block assembly 28 is provided with a floating drive halfnut 30 which advantageously engages with the leadscrew 26. The assembly also selectively engages with the rear end of the syringe plunger for expelling and discharge of the syringe contents. Towards this end, the pusher block assembly includes a block 32 that has a bottom end 34 provided with a pair of channels 36, 38 that receive guide rods 40, 42 which cooperate in causing the pusher block assembly 28 to move forwardly upon turning of the leadscrew 26 as a result of the meshing therewith by the floating drive halfnut 30. A lever 44 slides and is captured in the block 32. The spring 46 is secured at one end to the lower surface of leg 58 and fits around the head 57 of the shaft or actuator 59. At its other end, spring 46 is fixed to the inner peripheral flange 61 of lever 44. It is thus seen that by lifting lever 44 upwardly the shaft 59 will move upwardly in bore or opening 41 in block bottom end 34; and, consequently, the halfnut 30 will be moved upwardly into the bottom end 34 at the bottom of the pusher block 32. Spring 48 which is contained in housing block bottom end 34 continuously biases the floating halfnut 30 against the leadscrew 26. The upper spring 46 which surrounds the head 57 of the halfnut shaft or actuator 59 provides the force to keep the lever 44 and antisiphon catch 50 engaged with flange 52 of plunger 54 of syringe 56 shown in FIG. 2. In this manner, escape of plunger 54 is prevented which otherwise could result in a siphoning action. Spring 46 is biased between leg 58 and flange 61. Flange 61 also acts to engage head 57 to cause disengagement of the halfnut 30 and leadscrew 26.

Figure 6:
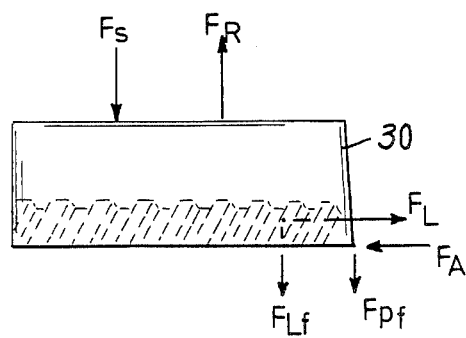
FIG. 6 is a vector force balance diagram of the invention showing diagramatically the interaction among the pusher block, halfnut and leadscrew.

FIG. 6 shows a simplified, two-dimensional force balance diagram which describes the floating halfnut of the invention. While the disclosed halfnut has three dimensional loading characteristics, these characteristics are not essential for a basic understanding of the invention. In the diagram $F_A$ refers to the axial force exerted by the pusher block 32 on halfnut 30 as a result of the driven load. $F_s$ refers to the force exerted by spring 48 on halfnut 32. $F_{Pf}$ refers to the frictional force existing between the pusher block 32 and the halfnut 30. $F_{Lf}$ refers to the frictional force between the halfnut 30 and the leadscrew 26. $F_L$ refers to the force in the axial direction exerted by the leadscrew 26 on the halfnut 30, and $F_R$ represents the total reaction attempting to separate the halfnut 30 from the leadscrew 26.

Experience with the disclosed invention has shown that the spring force $F_s$ required to maintain engagement is relatively small. A successful embodiment has a spring force of approximately 2 lbs.

A detailed engineering analysis has shown that placing the axial support force $F_A$ at or near the axis of the leadscrew (as two dimensionally represented in FIG. 6) results in a great reduction of $F_R$. This results correspondingly in a reduction of the spring force, $F_s$, required to maintain engagement. Frictional forces between the halfnut 30 and pusherblock 32, specifically and primarily $F_{Pf}$, and frictional forces between the halfnut 30 and leadscrew 26, specifically $F_{Lf}$, are essential to prevent separation of the halfnut 30 from the leadscrew 26. The theoretical analysis has shown that an advantageous balance of these forces exists which results in desirable engagement forces.

Reference is now made to the three dimensional characteristics of the leadscrew/halfnut combination. Leadscrew rotation will result in frictional forces normal to the corresponding contacting surfaces. However, halfnut 30 is free to float because neither the shaft 59 and head 57 nor the pusher block 32 are tightly guided or restrain the halfnut in directions normal to the separation direction. Because the halfnut of the present invention is allowed to float within the pusher block, symmetry of the aforementioned frictional forces is improved. Theoretically this results in lowering of the net force tending to separate the halfnut from the leadscrew. That is, $F_R$ has a minimal component due to leadscrew rotation and the associated surface friction The current embodiment has been estimated by the theoretical analysis to provide stable engagement regardless of the axial force $F_A$ and, further, requires no spring force $F_S$ to assure this engagement. That is, $F_{Pf}$ plus $F_{Lf}$ is estimated to be larger than $F_R$ for all $F_A$'s.

The floating halfnut of the present invention will develop forces due to the system friction and drive load which are greater than the separation forces that exist. The engagement forces are due to friction between the halfnut and leadscrew, and between the halfnut and pusher block. Further, a floating halfnut is so constructed that essentially no externally applied load is required to maintain engagement. This balance of forces is accomplished by properly choosing the supporting contact points among the halfnut, leadscrew, and pusher block, and by allowing the halfnut to float so that the leadscrew rotation does not add frictional separation forces.

Several features of the commercialized assembly help to improve the life of the halfnut. These self protecting features help to maintain the above described balance of forces throughout the product life. These features include, but are not limited to, a relatively long thread engagement length in the axial direction, thread engagement around fully one half of the leadscrew, a low wear carbon steel halfnut material, and a low friction, low wear plating on the halfnut.

The position of the pusher block 32 can be advantageously and quickly readjusted by disengaging the halfnut 30 with a minimum of manual effort because the spring force of spring 48 is at a minimum. In this respect the pusher block lever 44 is grasped and pulled.

Squeezing lever 44 towards the upper laterally extending leg 58 of block 32 will permit the syringe plunger flange 52 to be immediately released or permit the flange of a fresh syringe 56 to be engaged by the pusher block 28. The pusher block assembly 28 may then be freely moved along the guide rails 40, 42 for removal of a spent or emptied syringe 56 or reengagement by catch 50 of another flange 52 of a fresh filled syringe 56. Release of the lever 44 will pressure the antisiphon catch 50 to engage with the syringe plunger flange 52. Accordingly with the same action, coupling of the drive nut and antisiphoning is accomplished to thereby facilitate proper positioning of the syringe, pusher block and antisiphon mechanism one with the other. Furthermore, the antisiphon mechanism is designed to accept and capture a variety of syringe plunger flange sizes by allowing it to move to a capturing position independent of the drive nut engagement position. The syringe holder 60 advantageously permits the utilization of a wide variety of disposable syringes from various syringe manufacturers.

An end of syringe and an overpressure sensing assembly 80 which optionally may be combined with the drive of this invention permits the generation of a suitable signal when the contents of the syringe 56 has been fully discharged or an occlusion or other situation that would cause overpressure in the discharge line has occurred.

In use, a filled syringe with the selected drug or medicament is placed in the syringe holder 60. The pusher block assembly 28 is moved forwardly upon lifting of the lever 44 fully towards the leg 58 of the block 32. When the flange 52 of the plunger 54 is encountered the lever 44 is released to cause the halfnut 30 to reengage with the leadscrew 26 and the catch 50 captures the flange 52. The infusion pump 10 may be suspended from an IV pole and tubing from the syringe can be connected to the appropriate infusion site.

To summarize, the novel features of this invention include the method of floating the halfnut, and loading the halfnut 30 by the pusherblock 32 and the leadscrew 26 which provide an optimal force distribution and balance. Also of importance are the self-protection characteristics of the halfnut that prevent the load transmitting capabilities of the halfnut from being significantly impaired when misused. Advantageously, the present assembly provides lower engagement forces, increased safety, and/or simpler construction than the prior art halfnuts Thus the several aforenoted objects and advantages are most effectively attained Although a single somewhat preferred embodiment of the invention has been disclosed and described in detail herein, it should be understood that this invention is in no sense limited thereby and its scope is to be determined by that of the appended claims.

What is claimed is:

1. A syringe infusion pump comprising:
    a support;
    a syringe holder on the support;
    drive means on the support for driving the syringe plunger into the syringe barrel, said drive means includes a rotatably driven leadscrew on the support having a center line;
    an antisiphon and drive decoupling means on the support movable between a first position at which it is decoupled with the drive means and disengaged with the plunger of the syringe and a second position at which it is coupled with the drive means and engaged with the plunger of the syringe to prevent escape of the plunger and consequent siphoning action by the syringe, and the antisiphoning and drive decoupling means including a pusher block movable longitudinally on the support, a drive means engaging surface means on the block for meshing with the leadscrew, the drive means engaging surface means including a halfnut, the pusher block including floating means for permitting the drive engaging surface means to float freely to find the center line of the line leadscrew, the drive means engaging surface means including contacting points between the halfnut and pusher block spaced apart around the leadscrew substantially at the center line of the leadscrew with the contact points of the halfnut substantially near the center line normal to both the separation direction and the axis of the leadscrew thereby greatly reducing force mechanisms that attempt to separate the leadscrew and halfnut.

2. The invention in accordance with claim 1 wherein a relatively light first biasing means is on the block for applying relatively small forces between the halfnut and the leadscrew.

3. The invention in accordance with claim 2 wherein a shaft extends from the halfnut and the block and the shaft having an extremely loose fit that forms part of the floating means.

4. The invention in accordance with claim 3 wherein a lever is manually slidable in the block from the first position to the second position against the bias of a second biasing means biased between the block and the lever whereby when the lever approaches the second position the shaft moves to disengage the halfnut from the leadscrew and when the lever is released the shaft moves in to engagement with the halfnut and the leadscrew.

5. The invention in accordance with claim 1, wherein a pair of spaced longitudinally extending guide rails are on the support, the pusher block being slidable on the guide rails.

6. The invention in accordance with claim 1, wherein the pump is miniaturized, lightweight and portable with hanging means on the casing for hanging the pump on an IV pole.

7. A drive mechanism for a load comprising: a pusher block assembly having a halfnut, a leadscrew meshed therewith, the drive means engaging surface means including a half nut, the pusher block including floating means for permitting the drive engaging surface means to float freely to find the center line of the leadscrew, the drive means engaging surface means including contact points between the halfnut and pusher block spaced apart around the leadscrew substantially at the center line of the leadscrew with the contact points of the halfnut substantially near the center line normal to both the separation direction and the axis of the leadscrew thereby greatly reducing force mechanisms that attempt to separate the leadscrew and halfnut.

8. The invention in accordance with claim 7 wherein a relatively light first biasing means is on the block for applying relatively small forces betwen the halfnut and the leadscrew.

9. The invention in accordance with claim 8 wherein a shaft extends from the halfnut and the block and the shaft having an extremely loose fit that forms part of the floating means.

* * * * *